(12) United States Patent
Howell

(10) Patent No.: US 7,033,351 B2
(45) Date of Patent: *Apr. 25, 2006

(54) POWER SUPPLY FOR IDENTIFICATION AND CONTROL OF ELECTRICAL SURGICAL TOOLS

(75) Inventor: Thomas A. Howell, Saratoga, CA (US)

(73) Assignee: Starion Instruments Corporation, Saratoga, CA (US)

( * ) Notice: Subject to any disclaimer, the term of this patent is extended or adjusted under 35 U.S.C. 154(b) by 299 days.

This patent is subject to a terminal disclaimer.

(21) Appl. No.: 10/619,710

(22) Filed: Jul. 14, 2003

(65) Prior Publication Data

US 2004/0082944 A1    Apr. 29, 2004

Related U.S. Application Data

(63) Continuation-in-part of application No. 10/099,500, filed on Mar. 13, 2002, now Pat. No. 6,695,837.

(51) Int. Cl.
A61B 18/18    (2006.01)

(52) U.S. Cl. .......................................... 606/29; 606/32
(58) Field of Classification Search ................... 606/1, 606/29, 32–34, 41
See application file for complete search history.

(56) References Cited

U.S. PATENT DOCUMENTS

| | | | |
|---|---|---|---|
| 5,242,441 A | 9/1993 | Avitall | 606/41 |
| 5,383,874 A | 1/1995 | Jackson et al. | 606/1 |
| 5,593,406 A | 1/1997 | Eggers et al. | 606/29 |
| 5,651,780 A | 7/1997 | Jackson et al. | 606/1 |
| 5,792,138 A | 8/1998 | Shipp | 606/38 |
| 5,911,719 A | 6/1999 | Eggers | 606/31 |
| 6,017,354 A | 1/2000 | Culp et al. | 606/170 |
| 6,176,856 B1 | 1/2001 | Jandak et al. | 606/29 |
| 6,235,020 B1 | 5/2001 | Cheng et al. | 606/34 |
| 6,235,027 B1 | 5/2001 | Herzon | 606/51 |

Primary Examiner—Michael Peffley
Assistant Examiner—Pete Vrettakos
(74) Attorney, Agent, or Firm—K. David Crockett, Esq.; Crockett & Crockett

(57) ABSTRACT

An electronic circuit for identifying an electrical surgical tool and for providing a selectable constant current appropriate to the identified electrical surgical tool.

17 Claims, 5 Drawing Sheets

| Device | Rid | Vid | Output 40 | Output 41 | Output 42 |
|---|---|---|---|---|---|
| A | 1K Ohm | 4.5 | 1 | 1 | 1 |
| B | 10K Ohm | 2.5 | 0 | 1 | 1 |
| C | 51K Ohm | 0.83 | 0 | 0 | 1 |
| Foreign Device | Infinite | 0 | 0 | 0 | 0 |

POWER SUPPLY FOR IDENTIFICATION AND CONTROL OF ELECTRICAL SURGICAL TOOLS

This application is continuation-in-part of U.S. application Ser. No. 10/099,500 filed on Mar. 13, 2002 now U.S. Pat. No. 6,695,837.

FIELD OF THE INVENTIONS

The devices described below relate to power supplies intended to supply electrical power to medical instruments.

BACKGROUND OF THE INVENTIONS

Many electrical surgical devices are provided in the form of electrical surgical tools, such as a thermal cautery device, which can be plugged into a separate power supply. Typically, the power supplied to the electrical surgical tool must be carefully controlled; thus, the power supply includes circuitry to convert available AC power to AC, RF or DC power at the desired output power levels or frequencies. For example, Herzon, Thermal Cautery Surgical Forceps, U.S. Pat. No. 6,235,027 (May 22, 2001), shows thermal cautery forceps using a power supply to deliver a regulated current to the resistive heating elements in the forceps. Our own cautery instruments, such as the Starion® Thermal Cautery Forceps, which comprise forceps with resistive heating elements disposed on the grasping tips, are designed to work with our PowerPack Surgical Power Supply. Currently marketed versions of this power supply provide a current to the resistive heating elements depending on the heat load and temperature of the resistive heating device. In addition to these two devices, many electrical surgical instruments are currently marketed to address a variety of surgical techniques and the number of surgical instruments available has been growing.

The increase in the variety of surgical instruments has introduced a problem in medical-grade power supplies. Most power supplies can operate with different kinds of medical instruments, as long as an electrical connection can be established between the power supply and the instrument. However, a medical device manufactured by one company may perform slightly differently than expected when the medical device is used in conjunction with a power supply from another company. Since many medical procedures require precise control of the electrical properties of the medical device, a surgeon or doctor may unintentionally harm a patient when the surgeon uses a power supply and a medical device from different manufacturers. For example, though the Starion® PowerPack provides optimal power to the various Starion® electrical surgical tools for which it is intended, the use of connectors available to other medical device manufacturers may permit use of non-Starion® electrical surgical tools with the PowerPack. When used in combination with such third party electrical surgical tools, it is not possible to ensure that the optimal amount of power is delivered to the tool. Thus, the tool may not function as desired, with the result that the patient may be harmed. Thus, a medical-grade power supply is needed which operates only with the instruments made by that manufacturer and tested with that model of power supply.

SUMMARY

The methods and devices described below relate to a power supply that identifies an electrical surgical tool, such as a thermal cautery device, and provides power only to electrical surgical tools that are identified by the power supply. The power supply uses a device identification circuit and a constant current circuit to control the power output to an electrical surgical tool. The device identification circuit identifies whether an electrical surgical tool is designed to be used with that power supply. If the device identification circuit recognizes the electrical surgical tool, then the constant current circuit will provide a constant current, or electrical power, to the tool. In addition, the constant current circuit will provide the tool with the amount of power required by that particular device. If the device identification circuit does not recognize the device connected to the power supply, then the constant current circuit provides no power to the device.

DETAILED DESCRIPTION OF THE INVENTIONS

Figure 1:
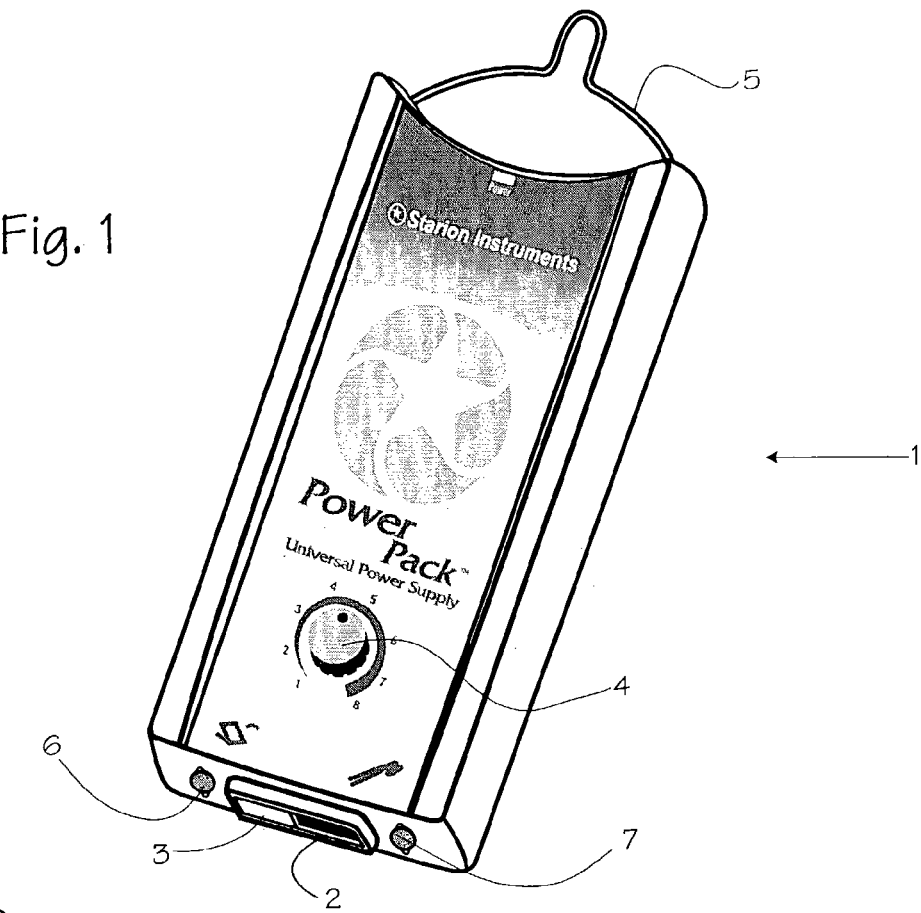
FIG. 1 illustrates the physical power supply box.

FIG. 1 illustrates a physical power supply box 1. The power supply box 1 is typically a non-sterile, reusable, AC powered device designed for use only with certain instruments, medical devices, electrosurgical devices or other electrical surgical tools such as thermal cautery devices. The power supply is connected to an AC power source. The power supply has an on-off switch 2, an AC power connector 3, an LED power indicator 4, a control knob 5 and a hanger 6 suitable for suspending the power supply on a support object, such as an IV pole. The power supply is also equipped with an input 7 for an interface board, control board or switches and an output 8 to the medical instrument. The supply has input requirements of 100 to 240 VAC at 50 to 60 Hz and at 80 W, has a maximum output of 32 VA, a no load voltage of 5V DC, and is operated at a duty cycle of about 5 seconds on and 10 seconds off. The output current is in the range of 2.4 A to 4.4 A, depending on which instrument is used and on the output desired by the user.

One version of the power supply, which is intended for use with cautery instruments, has three output heat levels: low, medium and high. The levels correspond to the desired heat output of the thermal cautery instrument's resistive heating element or elements, and correspond to current outputs of the power supply. A tone indicates the level of heat being applied to the cautery device. For example, a low tone indicates a low heat setting, an interrupted low tone indicates a medium heat setting and high tone indicates a high heat setting. Other devices have multiple heating elements and each element may have different heating levels. For medical devices with multiple settings or elements, the various settings and elements are adjustable. The adjustment of these settings or elements is typically facilitated by an interface board, or control board, that can switch between power levels or heating elements.

Figure 2:
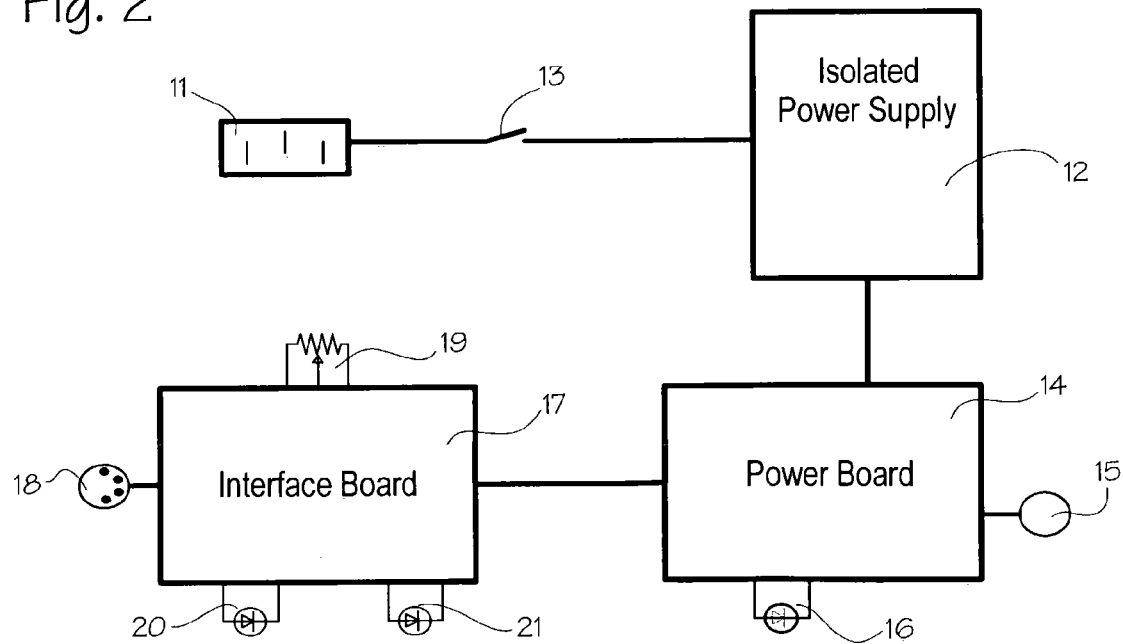
FIG. 2 is a block diagram of the power supply system.
Figure 3:
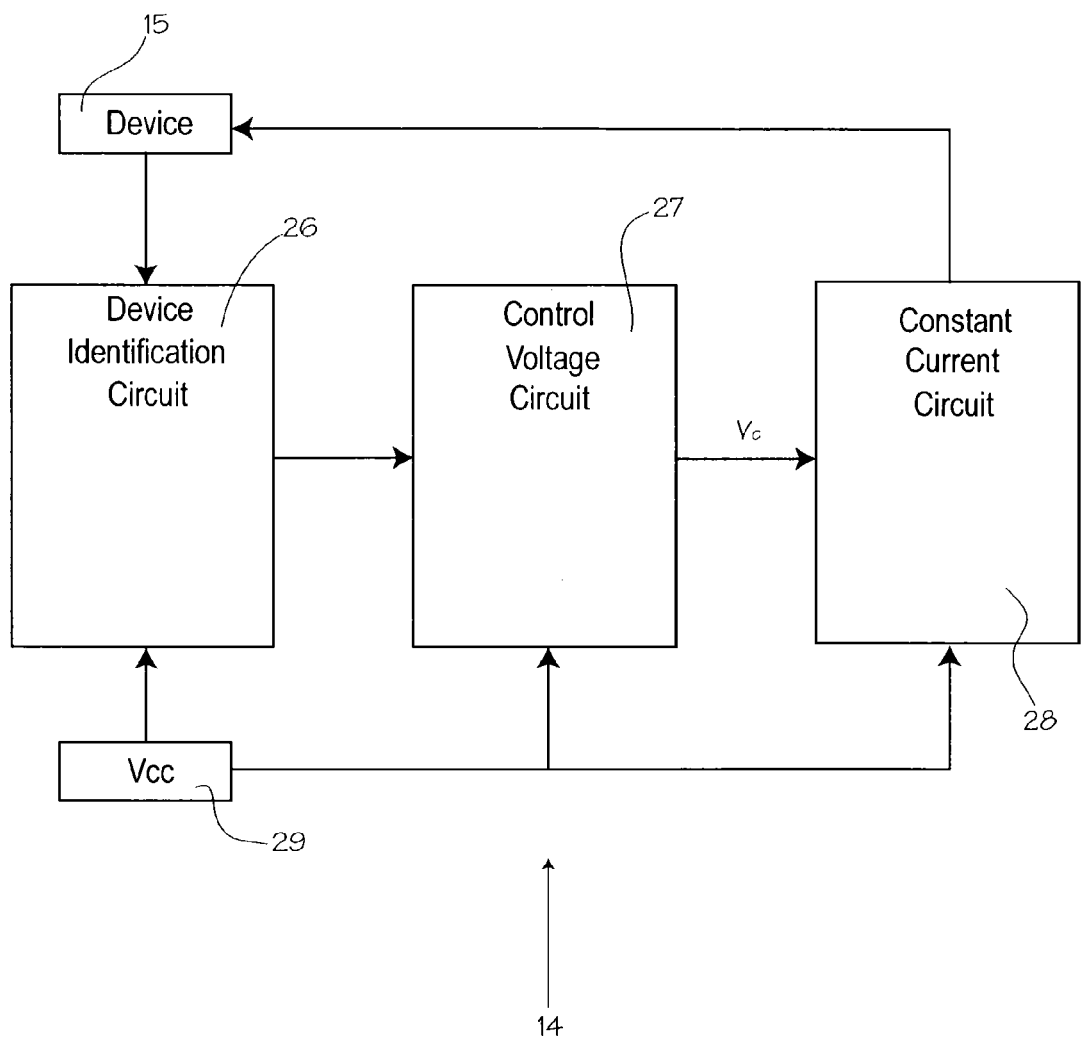
FIG. 3 is a block diagram of the power board system.

FIGS. 2 and 3 illustrate embodiments of the thermal cautery device, power supply and control system. The control system comprises the device identification circuit, the constant current circuit and, if used, the control voltage circuit and/or the user interface board. The control system thus comprises a means for connecting the switching power supply to the resistive heating element to provide power to the resistive heating element.

FIG. 2 is a block diagram of the power supply system and control system. Block 11 is the AC power input and is equipped with a power on/off switch 13. The AC power is connected to an isolated switching DC power supply 12, or AC to DC converter, through switch 13. However, the AC to DC converter can be replaced with an AC to low frequency AC converter, an AC to high frequency AC converter or an AC to low power AC converter. The isolated switching DC power supply 12 typically has an output of +5 volts DC. In addition, the isolated switching DC power supply is UL rated for heart contact, meaning that the output of the power supply can directly touch the patient. The DC power supply 12 is connected to a power board 14 which contains a constant current circuit, a control voltage circuit and a device identification circuit. The power board 14 is also connected to the electrical surgical tool 15, a power LED 16 indicating whether the power supply is on and an interface or control board 17. A user may provide input through the interface board to affect the settings of the power board and hence affect the operation of the thermal cautery device. The interface board 17 is optionally connected to a switch module 18, which typically has pedal or push button switches. The output of the switch module allows the user to select the level of power desired for a given procedure, or to select other modes of operation available to particular medical devices, when the switch module is connected to the control system. Alternatively, the switches can directly control the power level provided to the medical device. The interface board 17 is also attached to a current control knob or switch 19, a device LED 20 indicating whether an attached device is capable of functioning with the power supply, and a switch LED 21 that indicates that use of the switch module 18 is required. Note that other interface boards may be added to the power board.

FIG. 3 is a block diagram of the power board system. The power board 14 is conceptualized as three circuits: a device identification circuit 26, a control voltage circuit 27 and a constant current circuit 28. The electrical surgical device 15 is electrically connected to the device identification circuit 26 and receives current from the constant current circuit 28. A constant DC power source, $V_{cc}$ (item 29), is provided to all three circuits 27, 28 and 29, and is operated to supply power at about +5 volts DC. Note that other circuit blocks may be added, such as a circuit that provides a tone indicating the level of power running through the medical device or a circuit that facilitates the use of additional switches or pedals to control the power output of the power supply.

Figures 4, 5:
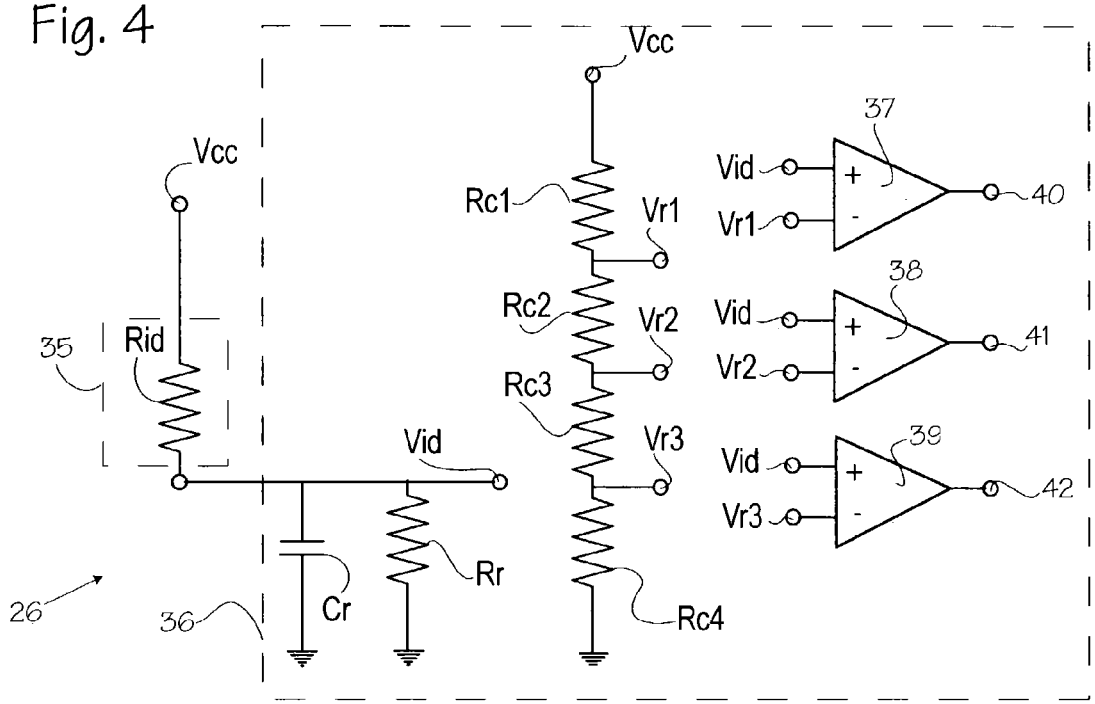
FIG. 4 is a circuit diagram of the device identification circuit.
FIG. 5 is a device identification table showing specific values of the identification resistor, the identification voltage and the comparator outputs for three distinct thermal cautery devices and a foreign device.

FIG. 4 is a circuit diagram of the device identification circuit 26, which includes all three diagrams shown in FIG. 4. The portion of the device identification circuit shown in area 35 (comprising the box 35 shown in phantom) contains the portion of the identification circuit located in the electrical surgical tool. The portion of the device identification circuit shown in area 35 comprises an identifying electrical component. In the embodiment shown in FIG. 4 the identifying electrical component is a resistor, though a capacitor, an inductor or other electrical component capable of uniquely identifying the cautery device may be used as the identifying electrical component. (In the case of a capacitor or an inductor, the device identification circuit would be modified to use the chosen identifying electrical component.) The portion of the identification circuit shown in area 36 (comprising the box 36 shown in phantom) is located in the power supply box. The various components of the device identification circuit can be placed in either the electrical surgical device or the power supply box. For example, all of the circuit could be inside the electrical surgical tool or all of the circuit could be placed inside the power supply box. However, if the identification resistor, $R_{id}$, is placed inside the power supply box, then means are provided such that a specific electrical surgical device plugs into a corresponding identification resistor. For example, a different outlet in the power supply box can be provided for each electrical surgical device. Alternatively, each electrical surgical device plug can have a different pin arrangement that plugs into a single outlet in the power supply box. In this case, the pin arrangement selects the proper identification resistor.

The device identification circuit can determine whether an electrical surgical device is plugged in or plugged in properly, whether the device is a device for which the power supply is designed, and which of a plurality of electrical surgical devices designed for use with the power supply is electrically connected to the power supply. In addition, the circuit of FIG. 4 constitutes a device identification means (or an electrical surgical device identification means or a thermal cautery device identification means), though the circuit may be varied in many respects. For example, the circuit of FIG. 4 is designed to identify three medical devices, though the circuit could add additional resistors to the resistor ladder and add additional comparators so that the device identification circuit can identify a plurality of electrical surgical devices or other kinds of electrical medical devices. In addition, capacitors can be added or subtracted from the circuit in order to create different kinds of filters. Also, the resistive heating element of the electrical surgical device can comprise the identification resistor as long as the resistive heating element of each electrical surgical device has a distinct resistance.

Referring again to FIG. 4, a voltage $V_{cc}$ is placed across a resistor, $R_{id}$, which is located in the plug of the medical device, and a reference resistor, $R_r$, connects to ground. An identifying voltage, $V_{id}$, develops across $R_r$. Note that $V_{id}$ varies with the value of $R_{id}$. $R_{id}$ is set by the manufacturer and is unique to a particular model of medical device. A capacitor, $C_r$, is placed in parallel with the reference resistor and operates as a low pass filter.

The identifying voltage, $V_{id}$, is sent to a comparator, which compares $V_{id}$ to a reference voltage, $V_r$. If the identifying voltage, $V_{id}$, is greater than the reference voltage, $V_r$, then the comparator (which can be a true comparator or an operational amplifier operated as a comparator) outputs a "1" signal. If the identifying voltage is less than the reference voltage, then the comparator outputs a "0" signal. The output of the comparator is provided to the control voltage circuit 27, which generates a control voltage, $V_c$. The control voltage determines, through the constant current circuit 28, the amount of power provided to the medical device.

The device identification circuit in FIG. 4 is designed to detect three kinds of medical instruments, each of which has a separate identifying resistor, $R_{id}$. Thus, the voltage cascade circuit has four comparison resistors, $R_{c1}$, $R_{c2}$, $R_{c3}$ and $R_{c4}$, placed in a resistor ladder. The resistor ladder produces a voltage cascade comprising a series of reference voltages. A reference voltage is taken between each of the reference resistors, the reference voltages comprising $V_{r1}$, $V_{r2}$ and $V_{r3}$. Each reference voltage is provided to the negative terminal of a distinct comparator; thus, $V_{r1}$ is provided to comparator 37, $V_{r2}$ is provided to comparator 38, and $V_{r3}$ is provided to comparator 39. On the other hand, the same identifying voltage, $V_{id}$, is provided to the positive terminal of each comparator. The output of each comparator, 40, 41 and 42, is provided to the control voltage circuit 27.

A first model of a medical instrument (device A) has an identifying resistor, $R_{id}$, with the smallest value. In this case the identifying voltage, $V_{id}$, will be higher than all three of the reference voltages. Thus, all three comparators will output a "1" signal. The fact that all three comparators output a signal is communicated through the control voltage circuit 27, which outputs a control voltage, $V_c$. The constant current circuit 28 then uses the control voltage to control electrical power to device A in an amount appropriate to device A.

Similarly, a second model of medical instrument (device B) will have an identifying resistor, $R_{id}$, of medium resistance. In this case the identifying voltage, $V_{id}$, will be lower than the first reference voltage, $V_{r1}$, but higher than the other two, $V_{r2}$ and $V_{r3}$. Thus, only comparators 38 and 39 will produce a "1" output. Accordingly, the constant current circuit 28 will recognize that device B is connected to the power supply. On the other hand, if a third model of medical instrument (device C) is connected to the power supply then $V_{id}$ will be less than $V_{r1}$ and $V_{r2}$, but greater than $V_{r3}$. In this case, only comparator 39 will report a "1" output and the constant current circuit 28 will recognize that device C is connected to the power supply. However, if $R_{id}$ is not present or does not have the correct value, then all of the comparators will output a "0" signal. In this case the control voltage will be "0" and then the constant current circuit will provide no power to the device. Thus, the power supply using the device identification circuit of FIG. 4 will only work with thermal cautery devices A, B and C.

The various values of $C_r$, $R_r$, $R_{id}$, $R_c$, $V_r$ and $V_{id}$ are set by the manufacturer and can have a wide range of values. In one embodiment $V_{cc}=+5V$, $C_r=10$ µF, $R_r=10$ KΩ, $R_{c1}=15$ KΩ, $R_{c2}=20$ KΩ, $R_{c3}=10$ KΩ and $R_{c4}=5.1$ KΩ. In this case $V_{r1}=3.5V$, $V_{r2}=1.5V$ and $V_{r3}=0.5V$. In addition, there are three thermal cautery devices designed by the manufacturer to operate with the power supply, the thermal cautery devices having $R_{id}$ values of 1 KΩ, 10 KΩ and 51 KΩ respectively. Furthermore, $V_{id}$ will have 3 different values, one for each thermal cautery device, as shown in the table of FIG. 5.

FIG. 5 is a device identification table showing the specific values of the identification resistor, the identification voltage and the comparator outputs for the three distinct thermal cautery devices and a foreign device. The columns in FIG. 5 reflecting comparator outputs 40, 41 and 42 show that each thermal cautery device has a unique set of comparator outputs. In the comparator output columns of FIG. 5, a "1" indicates an output signal of "1" and a "0" indicates an output signal of "0". Note that for each device (table row) $V_{r1}=3.5V$, $V_{r2}=1.5V$ and $V_{r3}=0.5V$ The table of FIG. 5 shows that when thermal cautery device A, with an $R_{id}$ of 1 KΩ, is plugged into the power supply then $V_{id}$ is 4.5V, which is higher than all three of the reference voltages, $V_{r1}$ (3.5V), $V_{r2}$ (1.5V) and $V_{r3}$ (0.5V). Thus, comparators 37, 38 and 39 all output a "1" signal and the system then knows that thermal cautery device A is plugged into the power supply. Applying similar logic, the system can tell if thermal cautery devices B or C are plugged into the system. However, if a foreign device is plugged into the system, or if no device is plugged into the system, then $R_{id}$ is infinity and thus $V_{id}=0$. If $V_{id}$ is 0 then $V_{id}$ is less than all three values of $V_r$; accordingly, all of the comparators will output a "0" signal and the constant current circuit 28 will provide no electrical power to the thermal cautery device.

The output of the device identification circuit, 40, 41 and 42, is fed into the input of the control voltage circuit 27. The control voltage circuit is a series of logic gates and analog circuits connected to the comparators and, optionally, to switches in the interface board. The logic gates, analog circuits and switches constitute a control voltage means. The control voltage circuit 27 outputs a control voltage, $V_c$, based on the output of the comparators and, optionally, based on the interface board switches 18. The control voltage that is output by the control voltage means is unique to a particular electrical surgical device that has been designed to work with the power supply. The switches and the control voltage circuit allow the user to select a control voltage from a set number of control voltages. The constant current circuit 28 uses the control voltage, $V_c$, to determine the amount of current delivered to the thermal cautery device.

Figure 6:
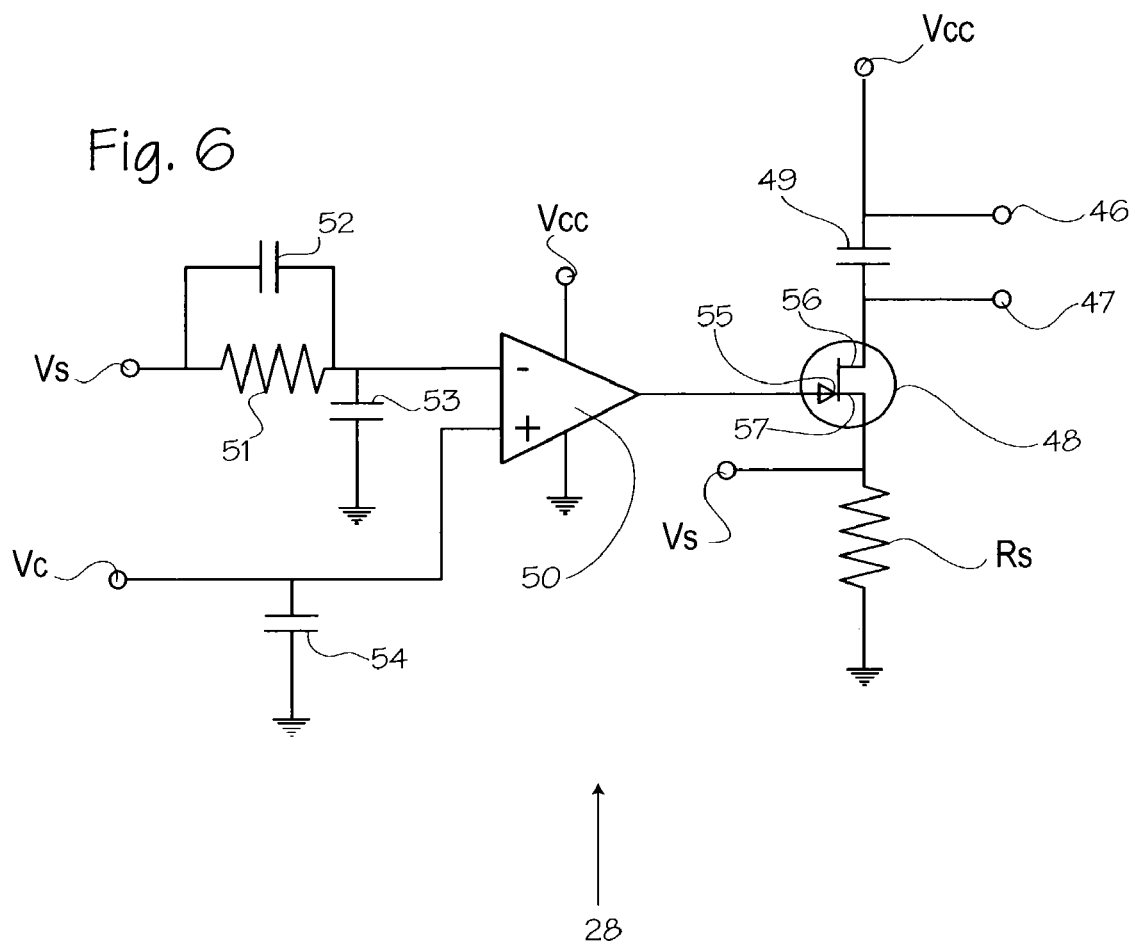
FIG. 6 is a circuit diagram of the constant current circuit.

FIG. 6 is a circuit diagram of the constant current circuit 28 which is operable to provide a constant current to a thermal cautery device. The main current path proceeds from $V_{cc}$ (typically +5 volts), through output plug (between terminals 46 and 47 when the terminals are electrically connected), through a power MOSFET 48 and finally through a sense resistor, $R_s$, used to sense the amount of current, $I_{main}$, flowing through the main current path. Other kinds of transistors can also be used, such as a JFET transistor or an NPN transistor (BJT transistor). A capacitor, 49, is placed between the terminals of the output plug and acts as a low pass filter. When current flows through the main current path, $R_s$ generates a sense voltage, $V_s$, proportional to the main current ($V_s=I_{main} \times R_s$) The circuit provides the sense voltage, $V_s$, to the negative terminal of an operational amplifier 50 through a low pass filter comprising resistor 51 and capacitors 52 and 53. The operational amplifier 50 is also connected to ground and to $V_{cc}$. The positive terminal of the operational amplifier is connected to the control voltage, $V_c$, through a low pass filter comprising capacitor 54. The operational amplifier compares the control voltage, $V_c$, to the sense voltage, $V_s$, and generates an output that controls the gate 55 of the power MOSFET 48. (The MOSFET drain 56 and source 57 are shown for convenience). The result is that the operational amplifier 50 adjusts the current flowing through the power MOSFET 48 until the sense voltage is equal to the control voltage ($V_s=V_c$). (The control voltage is based on the value of the identification resistor or other electrical identification component.) Thus, the constant current circuit 28 maintains the current at a steady level. The amount of current is set by the value of the sense resistor, $R_s$. For example, if the sense resistor, $R_s=0.1$ Ω and the control voltage, $V_c=0.1V$, then the main current, $I_{main}=1.0$ A.

The output plug (terminals 46 and 47) is electrically connected to the medical instrument's resistive heating elements, thus completing the electrical circuit. Accordingly, the current flowing through the main current path powers the medical instrument reliably and selectably.

The circuit shown in FIG. 6 can be varied in many respects. For example, the capacitors and resistors can take on different values, may be taken out of the circuit or other capacitors and resistors may be added to accomplish different filtering effects. In addition, the circuit can be similarly modified to provide different output currents for a given control voltage.

Figure 7:
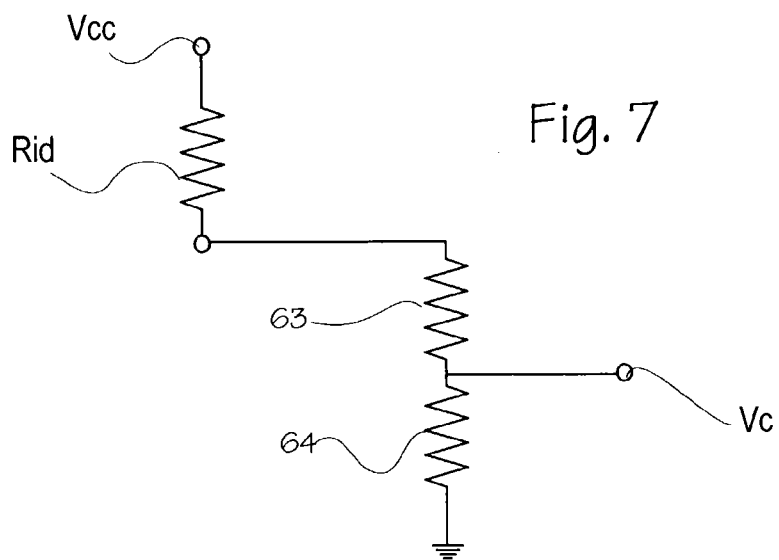
FIG. 7 is a circuit diagram of an alternate device identification circuit.

FIG. 7 is a circuit diagram of an alternate device identification circuit. A voltage, $V_{cc}$, is placed across a resistor, $R_{id}$, which is located in the plug of the electrical surgical tool. $R_{id}$ is set by the manufacturer and is unique to a particular thermal cautery device. A second resistor, 63, is connected to a control resistor, 64, which itself connects to ground. A control voltage, $V_c$, develops across control resistor 64 and $V_c$ varies with the value of $R_{id}$. The control voltage is provided to a constant current circuit, such as that shown in FIG. 5, which provides a constant current to the thermal cautery device. The output current is a function of $V_c$ and $R_{id}$ ($I_{output} = V_c/R_{id}$).

Figure 8:
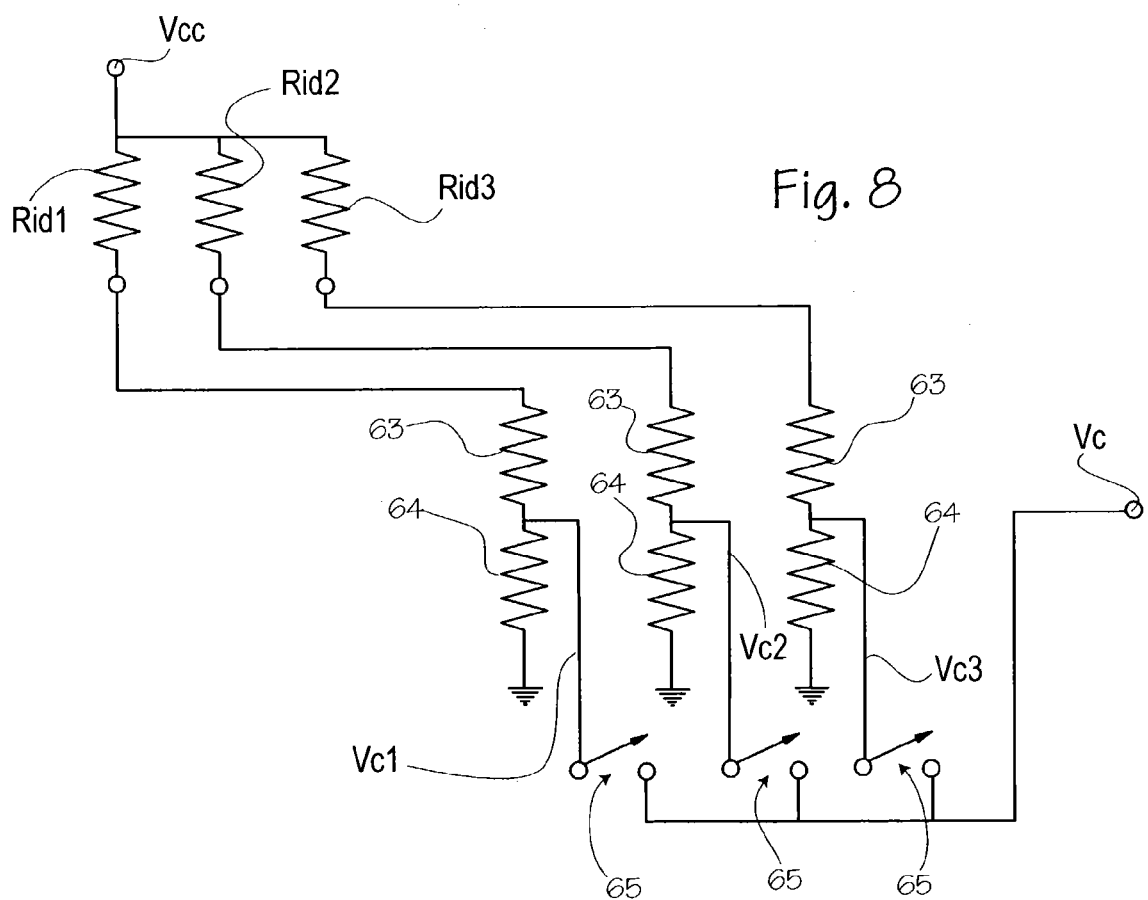
FIG. 8 is a circuit diagram of an alternate device identification circuit with switching.

FIG. 8 is a circuit diagram of an alternate device identification circuit with switching. Three circuits, similar to the one in FIG. 7, are combined using three different identification resistors, $R_{id1}$, $R_{id2}$ and $R_{id3}$, though resistors 63 and 64 have the same value in all three circuits. In addition, a switch 65 is provided in each individual circuit between the second resistor 63 and the control resistor 64. The switch 65 can be any kind of switch, such as a push button, a pedal or a knob. Selecting a switch chooses one of the control voltages, $V_{c1}$, $V_{c2}$ or $V_{c3}$ and sends that control voltage to a constant current circuit, such as the one shown in FIG. 6. The constant current circuit then provides a constant current to the electrical surgical tool appropriate to the particular thermal cautery device and appropriate to the switch or switch combination selected. In one embodiment the values of the components are $R_{id1}$=2.75 KΩ, $R_{id2}$=3.67 KΩ, $R_{id3}$=5.5 KΩ, $R_{63}$=10 KΩ, $R_{64}$=1 KΩ. Since V=IR then in this embodiment $I_{output}$=11 KΩ/$R_{id}$.

Depending on the design of the constant current circuit, control voltage circuit or other additional circuit, the combination of switches can control a variety of variables. For example, an electrical surgical tool may have one subcomponent that requires power. In this case the three switches control whether the device receives a high, medium or low amount of power. The constant current circuit shown in FIG. 6 can operate with the device identification circuit of FIG. 8 to perform this function.

Alternatively, other control voltage circuits can add additional capabilities when used in conjunction with the switch design of FIG. 8. For example, an electrical surgical tool can have three subcomponents, each of which require power. The three switches determine which, if any, of the subcomponents receive power. For other constant current circuits it is possible to use different combinations of open and closed switches. For the circuit shown in FIG. 8 there are eight possible switch combinations. Each combination of switch positions generates a distinct control voltage that can control different elements or power levels of the electrical surgical tool.

A plurality of switch circuits is also possible. In the case of a electrical surgical tool with three powered subcomponents, each of which having three power settings, then nine switches can control which subcomponent receives a given amount of power (depending on the design of the constant current circuit and control voltage circuits). In addition, a plurality of electrical surgical tools can be attached to the circuit, each electrical surgical tool having a unique identifying resistor. In this case the plurality of switches determine which, if any, of the devices are on. Finally, a plurality of switches can be provided on a circuit that accommodates multiple devices, each device having multiple powered subcomponents, each powered subcomponent having multiple power levels, and wherein different combinations of switch positions control different aspects of the device.

Although the methods, devices and circuits are described in relation to electrical surgical tools, the same methods, devices and circuits can be used with other kinds electrical devices where device identification is desired. For example, electrical surgical tools using DC, AC or RF power can use the device identification methods described above. Electrical surgical tools useable with the device identification circuit also include ablation devices, thermal ligation devices, thermal cautery devices, electrocautery devices and other kinds electro-medical instruments. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A system for performing thermal cautery system on body tissue, said system comprising:
    a thermal cautery device, said thermal cautery device comprising a resistive heating element mounted on means for pressing the resistive heating element into contact with body tissue;
    a switching power supply; and
    a control system comprising a means for operably connecting the switching power supply to the resistive heating element to provide power to the resistive heating element; and
    a means for identifying the thermal cautery device connected to the switching power supply, wherein the control system controls operation of the thermal cautery device based on the identity of the thermal cautery device; and
    wherein the means for identifying the thermal cautery device comprises:
        an identification resistor electrically connected to the thermal cautery device, said identification resistor having a pre-determined resistance value; and
        a reference resistor placed in series with the identification resistor when the thermal cautery device is electrically connected to the switching power supply, said reference resistor also electrically connected to ground such that an identifying voltage develops across the reference resistor when power is applied to the reference resistor and the identification resistor; and
        a comparison resistor electrically connected to the switching power supply and to ground, wherein a reference voltage develops across the comparison resistor when power is applied to the comparison resistor; and
        a comparator, wherein the positive terminal of the comparator is electrically connected to the identifying voltage and the negative terminal of the comparator is electrically connected to the reference voltage; wherein the comparator produces an output signal if the identifying voltage is higher than the reference voltage, said output signal indicating that a particular thermal cautery device is operably connected to the power supply.

2. The system of claim 1 wherein the thermal cautery device further comprises an identifying electrical component having a predetermined value and the control system further comprises a means for identifying the thermal cautery device based on the identifying electrical component.

3. The system of claim 2 wherein the control system provides power to the thermal cautery device only if the means for identifying a thermal cautery device identifies the thermal cautery device.

4. The system of claim 2 wherein the identifying electrical component is a resistor.

5. The electrical circuit of claim 4 wherein the resistor is chosen from the group consisting of about 1 KΩ, about 10 KΩ and about 51 KΩ.

6. The system of claim 1 further comprising a capacitor placed in parallel with the reference resistor.

7. The system of claim 1 wherein the identification resistor is chosen from the group consisting of about 1 KΩ, about 10 KΩ and about 51 KΩ.

8. A system for performing thermal cautery, said system comprising:
a thermal cautery device, said thermal cautery device comprising a resistive heating element mounted on means for pressing the resistive heating element into contact with body tissue; and
a means for providing a constant current;
and a means for operably connecting the resistive heating element to the means for providing a constant current in order to provide a constant current to the resistive heating element when power is applied to the system; and
wherein the means for providing a constant current comprises: a power source, wherein the resistive heating element of the thermal cautery device is electrically connected to the power source and to the drain of a power MOSFET; and a sense resistor electrically connected to the source of the power MOSFET and to ground, wherein a sense voltage develops across the sense resistor when power is applied to the sense resistor; and an operational amplifier, wherein the output of the operational amplifier is electrically connected to the gate of the power MOSFET, wherein the negative terminal of the operational amplifier is electrically connected to the sense voltage, and wherein the positive terminal of the operational amplifier is electrically connected to a control voltage such that when power applied to the system the circuit will adjust the current until the sense voltage equals the control voltage.

9. The system of claim 8 further comprising:
a control system operable to set the control voltage based on the input of a means for identifying the thermal cautery device.

10. The system of claim 9 wherein the control system provides power to the thermal cautery device only if the means for identifying a thermal cautery device identifies the thermal cautery device.

11. The system of claim 9 wherein the power source comprises a switching power supply.

12. The system of claim 9 wherein the means for identifying the thermal cautery device is based on an identifying electrical component.

13. The system of claim 12 wherein the identifying electrical component is a resistor.

14. The system of claim 13 wherein the resistor is chosen from the group consisting of about 1 KΩ, about 10 KΩ and about 51 KΩ.

15. The system of claim 9 wherein the means for identifying the thermal cautery device comprises:
an identification resistor electrically connected to the thermal cautery device, wherein the identification resistor of the thermal cautery device comprises a predetermined resistance value and is capable of receiving power from the switching power supply;
a reference resistor placed in series with the identification resistor when the thermal cautery device is electrically connected to the switching power supply, said reference resistor also electrically connected to ground such that an identifying voltage develops across the reference resistor when power is applied to the reference resistor and the identification resistor;
a comparison resistor electrically connected to the switching power supply and to ground, wherein a reference voltage develops across the comparison resistor when power is applied to the comparison resistor;
a comparator, wherein the positive terminal of the comparator is electrically connected to the identifying voltage and the negative terminal of the comparator is electrically connected to the reference voltage;
wherein the comparator produces an output signal indicating the presence of a particular thermal cautery device when power is applied to the circuit if the identifying voltage is higher than the reference voltage;
wherein the comparator output comprises the control voltage.

16. The system of claim 15 further comprising a capacitor placed in parallel with the reference resistor.

17. The system of claim 15 wherein the identification resistor is chosen from the group consisting of about 1 KΩ, about 10 KΩ and about 51 KΩ.

* * * * *